US010041105B2

(12) United States Patent
Li

(10) Patent No.: US 10,041,105 B2
(45) Date of Patent: Aug. 7, 2018

(54) METHODS AND DEVICES FOR DETECTION OF RESISTANCE TO AN ENZYME INHIBITOR

(71) Applicant: CELLEX, INCORPORATED, Cary, NC (US)

(72) Inventor: Xingxiang Li, Cary, NC (US)

(73) Assignee: CELLEX, INCORPORATED, Cary, NC (US)

( * ) Notice: Subject to any disclaimer, the term of this patent is extended or adjusted under 35 U.S.C. 154(b) by 0 days.

(21) Appl. No.: 14/684,938

(22) Filed: Apr. 13, 2015

(65) Prior Publication Data

US 2015/0291997 A1   Oct. 15, 2015

Related U.S. Application Data

(60) Provisional application No. 61/979,827, filed on Apr. 15, 2014.

(51) Int. Cl.
| | | |
|---|---|---|
| *C12Q 1/34* | (2006.01) | |
| *G01N 21/76* | (2006.01) | |
| *G01N 21/64* | (2006.01) | |

(52) U.S. Cl.
CPC ............... *C12Q 1/34* (2013.01); *G01N 21/64* (2013.01); *G01N 21/76* (2013.01); *G01N 21/763* (2013.01); *G01N 2333/11* (2013.01); *G01N 2333/986* (2013.01)

(58) Field of Classification Search
CPC .................................................. G01N 2333/11
See application file for complete search history.

(56) References Cited

U.S. PATENT DOCUMENTS

| | | | |
|---|---|---|---|
| 7,897,330 B2 * | 3/2011 | Patel ................. | B01L 3/50273 435/4 |
| 8,481,281 B2 | 7/2013 | Demirev et al. | |
| 2008/0102483 A1 | 5/2008 | Black et al. | |
| 2011/0189655 A1 | 8/2011 | Li et al. | |
| 2011/0245105 A1 | 10/2011 | Citri | |
| 2011/0300552 A1 | 12/2011 | Demirev et al. | |
| 2013/0288356 A1 | 10/2013 | Demirev et al. | |
| 2014/0134656 A1 | 5/2014 | Dortet et al. | |

FOREIGN PATENT DOCUMENTS

| | | |
|---|---|---|
| EP | 1160332 A1 | 12/2001 |
| WO | 02/055015 A2 | 7/2002 |
| WO | 2005075670 A2 | 8/2005 |
| WO | 2009051838 A1 | 4/2009 |
| WO | 2012175637 A1 | 12/2012 |

OTHER PUBLICATIONS

Buxton et al. Analytical Biochemistry, 2000, 280:291-3000.*
Kawai et al. J of Infection, 2009, 59:207-212.*
Barrett et al. PLoS One, 2011, 6(8)e23627, pp. 1-9.*
International Search Report related to PCT Patent Application No. PCT/US2015/025591 dated Jun. 19, 2015.
N. T. Wetherall et al. "Evaluation of Neuraminidase Enzyme Assays Using Different Substrates to Measure Susceptibility of Influenza Virus Clinical Isolates to Neuraminidase Inhibitors: Report of the Neuraminidase Inhibitor Susceptibility Network" Journal of Clinical Microbiology, (2003), pp. 742-750.
Henju Marjuki et al. "Bioluminescence-Based Neuraminidase Inhibition Assay for Monitoring Influenza Virus Drug Susceptibility in Clinical Specimens" Antimicrobial Agents and Chemothereapy, (2013), vol. 57, No. 11, pp. 5209-5215.
Supplementary European Search Report dated Aug. 21, 2017 by the European Patent Office in corresponding EP Application No. 15780015.2—9 pages.
Cormican, Martin G., et al., "Detection of Extended-Spectrum B-Lactamase (ESBL)—Producing Strains by the Etest ESBL Screen," Journal of Clinical Microbiology, Aug. 1996, p. 1880-1884, vol. 34, No. 8—XP-002469590.
Noyal, M.J.C., et al., "Simple screening tests for detection of carbapenemases in clinical isolates of nonfermentative Gram-negative bacteria," Indian J. Med. Res., Jun. 2009, p. 707-712, vol. 129—XP002772808.

* cited by examiner

*Primary Examiner* — Bin Shen

(74) *Attorney, Agent, or Firm* — Millen White Zelano and Branigan, PC; Csaba Henter

(57) ABSTRACT

Embodiments described herein relate to assay methods and kits for detecting resistance of any enzyme to its inhibitor due to functional alteration of the enzyme, comprising, conducting two or more reactions with two or more reagent mixes optionally containing substrates for the enzyme. The mixes are substantially similar, except that one contains no enzyme inhibitor whereas the others contain an enzyme inhibitor being tested for resistance. The ratio of the signal from the reaction with an inhibitor to that from a reaction without an inhibitor is used to indicate whether the enzyme is resistant to the enzyme inhibitor and also determine the susceptibility or resistance of the enzyme to various inhibitors and further identify enzyme variants. Embodiments further relate to assay methods comprising only two reactions—one conducted in a mix containing the inhibitor and the other without the inhibitor. Further included are devices for conducting such assays.

30 Claims, 4 Drawing Sheets

FIG. 1

METHODS AND DEVICES FOR DETECTION OF RESISTANCE TO AN ENZYME INHIBITOR

CROSS-REFERENCE TO RELATED APPLICATION

This application claims priority to U.S. Provisional Application No. 61/979,827, filed Apr. 15, 2014, the entire disclosure of which is hereby incorporated by reference.

GOVERNMENT FUNDING

This invention was made in part with government grants awarded by the National Institutes of Health of the United States.

SEQUENCE LISTING

The instant application contains a Sequence Listing which has been submitted electronically in ASCII format and is hereby incorporated by reference in its entirety. Said ASCII copy, created on Apr. 15, 2015, is named CELLEX-0020_SL.txt and is 997 bytes in size.

TECHNICAL FIELD

The present invention relates to a method and device for use in detection for resistance of an enzyme in a sample to its inhibitor. When the enzyme inhibitor is a pharmacological drug, the method can be used to detect drug resistance. The methods may be applied to detection of resistance to any enzyme inhibitor when the resistance is caused by functional alteration to the enzyme. The method can also be used to differentiate enzyme variants with respect to resistance to various inhibitors of an enzyme. The invention also includes a detection device for use with the assays.

BACKGROUND

Enzymes in biological systems perform important functions for the biological systems and, therefore, are important targets for pharmacological intervention. Many enzyme inhibitors have been developed and used to intervene with the biological processes catalyzed by the enzymes. An enzyme inhibitor is a molecule, which binds to enzymes and decreases their activity. The binding of an inhibitor can stop a substrate from entering the enzyme's active site and/or hinder the enzyme from catalyzing its reaction. Inhibitor binding is either reversible or irreversible, causing reversible or irreversible inhibition. Reversible inhibition can be competitive, non-competitive or a combination of the two. Irreversible inhibitors bind to the enzyme normally through an irreversible covalent bond.

Many enzyme inhibitors have been developed and successfully used as pharmaceutical drugs for treatment of various diseases. Imatinib mesylate, which is the active ingredient of the brand name drug GLEEVEC™, inhibits a protein-tyrosine kinase, over-expression of which causes chronic myeloid leukemia. The enzyme inhibitor inhibits the activity of the protein-tyrosine kinase and thus effectively treats the leukemia. Specific protease inhibitors have also been successfully used to treat infections of human immunodeficiency virus (HIV) and hepatitis C virus (HCV). Use of antibiotics to treat bacterial infections has saved countless lives. The mainstay of pharmaceutical antibiotics is beta lactams, which include penicillins, cephalosporins, monobactams, and carbapenems. However, many bacterial species develop beta lactamases, which degrade these beta lactam antibiotics and thus confer bacterial resistance to these antibiotics. Several beta lactamase inhibitors, including clavulanate, sulbactam, and tazobactam, have been developed to overcome bacterial resistance to antibiotics.

Likewise, current mainstay of therapeutic intervention for influenza is a new class of pharmaceuticals known as neuraminidase inhibitors, which inhibit the activity of influenza viral neuraminidase. Since influenza viral neuraminidase is an essential enzyme for both Type A and Type B influenza viruses, these drugs are efficacious in treating influenza. Two such drugs—oseltamivir and zanamivir—have now been approved by many countries for treating patients with influenza. Oseltamivir and zanamivir are the active ingredients of anti-influenza drug TAMIFLU and RELENZA, respectively.

Therapeutic use of these enzyme inhibitors can lead to genetic alteration of the target enzymes such that the inhibitors could no longer effectively inhibit the enzymes, a phenomenon commonly known as drug resistance. For example, use of HIV protease inhibitors can quickly lead to selection of mutations in the protease gene, which confer resistance of HIV to these inhibitors. Similarly, influenza virus mutants that confer resistance to either oseltamivir, an important drug for treatment of influenza, have appeared. During the 2008/2009 seasonal influenza, nearly all of the H1N1 isolates circulating in U.S. were resistant to oseltamivir.

It is thus important to have rapid and easy-to-use tests for detection of resistance to these enzyme inhibitors. Resistance to enzyme inhibitors is normally measured by $IC_{50}$, the inhibitor concentration at which 50% of the enzyme activity is inhibited. Measurement of an $IC_{50}$ value of an inhibitor for an enzyme normally involves the use of an enzyme inhibition assay comprising 8 to 12 reactions, which contain increasing concentrations of the inhibitor to be tested. The $IC_{50}$ value is indicative of whether the enzyme is resistant, or the degree of susceptibility, to the inhibitor, particularly when compared to that of a known wild-type or mutant enzyme. For example, the oseltamivir carboxylate $IC_{50}$ value of a wild-type H1N1 influenza virus is normally less than 5 nM whereas that of a mutant carrying an H274Y mutation in the neuraminidase gene is normally greater than 50 nM.

Because an enzyme inhibition assay normally uses 8-12 reactions, it is cumbersome and expensive to measure the $IC_{50}$. Consequently, the enzyme inhibition assay has not been widely used for clinical purposes. In an embodiment of the present invention, only two reactions, one with the drug and another without the drug, are sufficient in identifying drug resistance by simply using the signal ratio of the two reactions as the indicator. The two reaction assay greatly simplifies the drug resistance detection assays. Use of a detection device with dual sample reading capability further simplifies the assay procedure.

SUMMARY OF THE INVENTION

A few of the many embodiments encompassed by the present description are summarized in the following paragraphs. The paragraphs are self-referential. In particular, the phase "in accordance with any of the foregoing or the following" used in the paragraphs refers to the other paragraphs. The phrase means in the following paragraphs embodiments herein disclosed include both the subject matter described in the individual paragraphs taken alone and the subject matter described by the paragraphs taken in combination. In this regard, it is explicitly applicant's purpose in setting forth the following paragraphs to describe various aspects and embodiments particularly by the paragraphs taken in combination. That is, the paragraphs are a compact way of setting out and providing explicit written description of all the embodiments encompassed by them individually and in combination with one another and, accordingly, the subject matter set out in any of the following paragraphs, alone or together with any other subject matter of any one or more other paragraphs, including any combination of any values therein set forth taken alone or in any combination with any other value set forth may be claimed. Should it be required, all of the combinations herein set forth may be recited in this application or in any successor applications having benefit of this application.

In an embodiment, the method disclosed in the present invention is an enzymatic assay comprising two reactions. The two reactions are enabled by two reagent mixes (herein frequently referred to as Reagent Mix I and Reagent Mix II). The two reagent mixes are substantially the same except that one of the reagent mixes, e.g., Reagent Mix II, contains the enzyme inhibitor or its active form at an appropriate concentration. The reagent mixes contain an enzyme substrate, which upon interaction with the enzyme in a sample causes the increase of signal, thereby indicating the presence of the enzyme in the sample. The enzyme substrate in the reagent mixes can be chromogenic, fluorogenic, chemiluminescent or of producing other measurable signals. In certain embodiments, the enzyme substrate is a chemiluminescent substrate as chemiluminescent reactions generally have wider linear range.

Since the enzyme activity is inhibited or partially inhibited in the reaction which contains the inhibitor (e.g., Reagent Mix II), the signal in that reaction is reduced. The level of signal reduction in the reaction with the enzyme inhibitor in comparison to the signal of the reaction without the inhibitor is indicative of the level of resistance or susceptibility of the enzyme to the inhibitor. The level of signal reduction can be expressed as a signal ratio in various forms. The cutoff value of the signal ratio for an enzyme can be determined empirically by testing a large number of samples.

Appropriate samples for use in detection of resistance to an enzyme inhibitor include, but are not limited to, purified enzyme, partially purified enzyme and a sample containing the enzyme activity. If the enzyme is contained within cells or as part of virus, the cells or the virus may need to be lysed to release the enzyme or to enable reaction reagents in contact with the enzyme.

Since two reactions enabled by Reagents Mixes I and II, respectively, are used to detect resistance of an enzyme to an inhibitor, a signal detection device capable of simultaneously detecting the signals from the two reactions is provided in this invention.

In certain embodiments, detection for resistance to more than one inhibitor of an enzyme is preferred as enzyme variants with different inhibitor resistance profiles may exist. In this case, several versions of inhibitor-containing reagent mix can be formulated; each of the inhibitor-containing reagent mix contains a unique inhibitor to be tested. For example, there are a number of pharmaceutical drugs for treatment of influenza (e.g., oseltamivir and zanamivir), which are the inhibitors of influenza viral neuraminidase. To detect resistance of an influenza virus to both oseltamivir and zanamivir in an assay, two versions of inhibitor-containing reagent mixes can be formulated so that one of them contains oseltamivir while the other contains zanamivir. Therefore, this type of assays consists of one reagent mix, which contains no inhibitor, and several versions of reagent mixes, each of which contains a distinct enzyme inhibitor.

In other embodiments, different resistance profiles to inhibitors for an enzyme are used to differentiate variants of an enzyme. For example, numerous bacterial species carry beta lactamases, which may have various profiles of resistance to beta lactamase inhibitors. For example, assays can be formulated according to present invention to detect and differentiate certain beta lactamase types such as carbapenemase, which can degrade carbapenems, a class of antibiotics often used as the "last-resort" antibiotics. Infection of a carbapenemase-producing organism (CPO) can lead to high rates of mortality and morbidity as these bacterial species are often resistant to most other antibiotics. Thus, identification of a CPO is important for clinical and public health purpose. According to the present invention, two reagents can be formulated so that Reagent Mix I contains necessary reagents for detection of any beta lactamase while Reagent Mix II contains a carbapenem in addition to all of the ingredients in Reagent Mix I. While above cutoff signal of Reagent Mix I indicates the presence of a beta lactamase (including a carbapenemase) in the sample, above cutoff ratio of Reagent Mix II signal to Reagent Mix I signal indicates that the beta lactamase in the sample is a carbapenemase, thereby detecting and differentiating beta lactamases.

Since the signal ratio of Reagent Mix I to Reagent Mix II (or Reagent Mix II to Reagent Mix I) is used to determine the susceptibility/resistance of an enzyme to an inhibitor or differentiate variants of an enzyme (e.g., carbapenemase vs. common beta lactamase), it is important that the difference in signal levels in the two reagent mixes reflects only inhibition of the enzyme by the inhibitor present in Reagent Mix II, not variation between the two reagent mixes. One embodiment of the present invention uses two reagent beads, a master mix bead and an inhibitor bead, to minimize the variation of signal ratio due to reagent variations. The master mix beads contain ingredients which enable signal production in the presence of the enzyme while the inhibitor beads contain an appropriate concentration which can sufficiently inhibit enzyme activity. In certain embodiments, same lots of master mix bead and inhibitor beads are used in both Reagent Mix I and Reagent Mix II in a kit. For example, one master mix bead from the same lot is filled into both Reagent Mixes I and II vials while an inhibitor bead is filled into Reagent Mix II vial; the Reagent Mix I and II vials such prepared are then packaged into a test kit and used for sample testing. Individuals skilled in the art can develop the formulations and processes for production of reagent beads.

Embodiments of the present invention include, but are not limited to, the following aspects:

Aspect 1. A method for detection of resistance of an enzyme in a sample to an inhibitor, the method comprising:
  a) an assay with two or more reactions enabled by two or more reagent mixes, one of which contains no inhibitor while the other contains at least an inhibitor of said enzyme at an inhibitory concentration; and
  b) use of the signal ratio, or a multiple of the signal ratio, of signal from the reaction with inhibitor to that from the reaction without inhibitor to indicate the resistance or susceptibility of the enzyme to the inhibitor;

Aspect 2. The method according to Aspect 1, wherein said reagent mixes are substantially similar except that one contains no enzyme inhibitor whereas the other contains an enzyme inhibitor at an inhibitory concentration;

Aspect 3. The method according to Aspect 1, wherein said reagent mixes contain a substrate for the enzyme to be tested;

Aspect 4. The method according to Aspect 3, wherein said substrate is a chromogenic, fluorogenic or chemiluminescent substrate;

Aspect 5. The method according to Aspect 4, wherein said chemiluminescent substrate is a dioxetane derivative;

Aspect 6. The method according to Aspect 4, wherein said chemiluminescent substrate is a luciferin derivative;

Aspect 7. The method according to Aspect 1, wherein said substrate is an influenza viral neuraminidase substrate for detection of influenza viral neuraminidase activity in a sample;

Aspect 8. The method according to Aspect 1, wherein said substrate is a beta lactamase substrate for detection of beta lactamase activity in a sample;

Aspect 9. The method according to Aspect 1, wherein said inhibitor at sufficient concentrations inhibits the activity of susceptible influenza viral neuraminidase;

Aspect 10. The method according to Aspect 1, wherein said inhibitor at sufficient concentrations inhibits the activity of susceptible bacterial beta lactamase;

Aspect 11. The method of Aspect 9, wherein the inhibitor is one of the following: oseltamivir carboxylate, zanamivir, peramivir and laninamivir;

Aspect 12. The method of Aspect 10, wherein the inhibitor is one of the following: clavulanate, sulbactam, tazobactam, avibactam, ion chelators and a beta lactam antibiotic;

Aspect 13. The method of Aspect 12, wherein the inhibitor is one of the following: extended-spectrum cephalosporins, carbapenems, and oxacillin or its derivatives;

Aspect 14. A method for detection of resistance of an enzyme in a sample to an inhibitor, the method comprising:
  a) an assay with two reactions enabled by two reagent mixes, one of which contains no enzyme inhibitor while the other contains an inhibitor;
  b) use of signal ratio, or a multiple of the signal ratio, of signal from the reaction with an inhibitor to that from the reaction without the inhibitor to indicate resistance or susceptibility of the enzyme to the inhibitor; and
  c) a signal detection device containing two detection chambers to accommodate signal detection of the two reactions;

Aspect 15. The method of Aspect 14, wherein said device is capable of detecting the signals of the two reactions, computing the signal ratio and interpreting the test results;

Aspect 16. The method of Aspect 14, wherein each of said two detection chambers contains a signal sensor.

Aspect 17. A reagent kit for detecting the resistance or susceptibility of an enzyme to an inhibitor, comprising, in one or separate packages, a plurality of reagent mixes each comprising a substrate that is processed by said enzyme to yield a detectable signal, wherein a first reagent mix contains no inhibitor while a second reagent mix contains an inhibitor of said enzyme at a concentration effective to inhibit said enzyme, wherein said first and second reagent mixes contain a master mix reagent bead, which enable signal production in the presence of the enzyme, and said second reagent mix contains an additional reagent bead with an enzyme inhibitor.

Aspect 18. The kit of aspect 17, further comprising a chromogenic, fluorogenic or chemiluminescent substrate optionally together with instructions.

BRIEF DESCRIPTION OF THE DRAWINGS

Various features and advantages of the embodiments herein described can be fully appreciated as the same becomes better understood when considered in light of the accompanying drawings:

FIG. 1 is a diagram showing the correlation between R-Factor values and proportions of oseltamivir carboxylate (OC) resistant influenza virus in a mixture of OC resistant and susceptible virus. Oseltamivir susceptible virus (A/H1N1p/CA/07/2009) was mixed with an increasing amount of oseltamivir resistant virus (A/H1N1p/NC/39/2009) and tested with Reagent Mixes I and II as described in the present invention. Reagent Mixes I and II were identical except that Reagent Mix II contained the inhibitor oseltamivir carboxylate. The R-Factor values were calculated as 10 times the signal ratio of Reagent Mix II signal to Reagent Mix I signal. The R-Factor values were plotted against the proportion of OC resistant virus in the sample.

FIG. 2 is a diagram showing the correlation of R-Factor values and $IC_{50}$ values of influenza virus isolates consisting of both OC resistant and susceptible viruses. Influenza virus isolates resistant or susceptible to oseltamivir carboxylate (OC) were tested using the two reaction assay as described in the present invention. The R-Factor values were plotted against the IC50 values (nM) of the virus. The influenza virus isolates were separated into two distinct groups: an OC susceptible group exhibiting low IC50 values and low R-Factor values and an OC resistant group exhibiting high IC50 values and high R-Factor values.

FIG. 3 shows the reaction kinetics of a beta lactamase assay used for detection of antibiotic resistance.

FIG. 4 shows components of the kits of the invention which are used in detection of flu virus drug resistance. The exemplified kit ensures that the reagents for signal production are very similar and that the signal ratio of Reagent Mix II to Reagent Mix I is optimal for detection. Shown are two types of reagent beads: the master mix bead and inhibitor bead. The kits utilize the same master mix beads from the same manufacturing lot for both Reagent I and Regent II, with Reagent II containing an extra inhibitor bead, as shown.

DETAILED DESCRIPTION OF THE INVENTIONS

The present invention discloses a method for determination of resistance of an enzyme to its inhibitor. The method uses an assay comprising two reactions enabled by two reagent mixes. In one embodiment, the assay can be completed within 60 minutes and most likely within 30 minutes. The two reagent mixes enable detection of enzymatic activity in the sample. The two reagent mixes are substantially the same except that one of the reagent mixes contains an appropriate concentration of an enzyme inhibitor or its active form. The signal from the reaction containing the enzyme inhibitor is substantially reduced if the enzyme is susceptible to the inhibitor. On the other hand, a significant level of signal from the reaction containing the inhibitor remains if the enzyme is resistant to the inhibitor. The signal ratio of the two enzyme reactions is indicative of whether the

Figure 2:
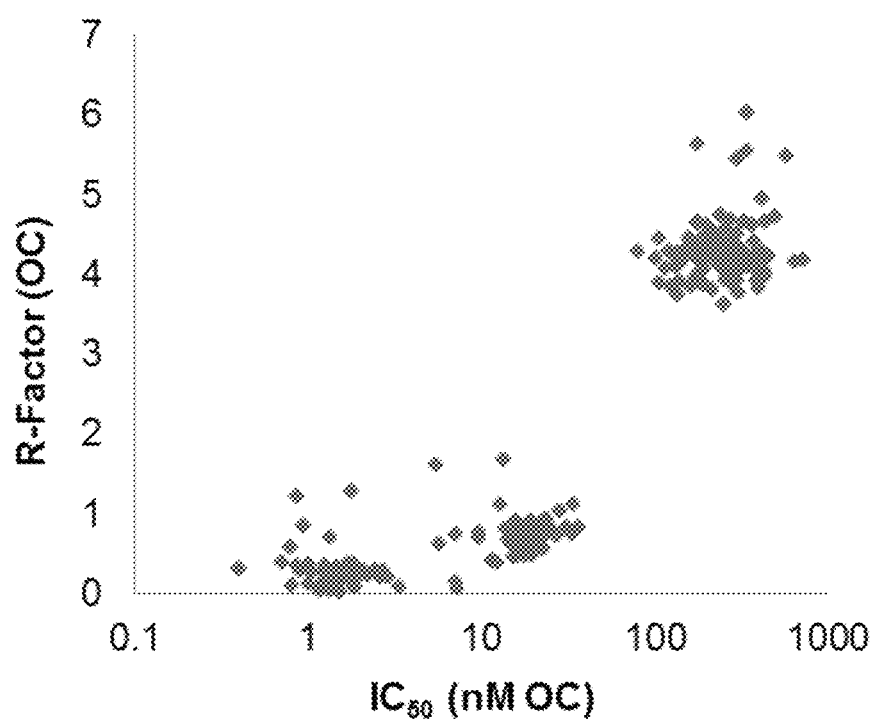

enzyme is resistant to the inhibitor. When the inhibitor is a pharmaceutical drug, the assay can be used to detect pharmaceutical drug resistance.

The reagent mixes contain an enzyme substrate, which can specifically interact with the enzyme and cause increase or otherwise change in signal in terms of signal intensity (e.g., chemiluminescent signal intensity) or signal profile (e.g., changes in retention time in an HPLC chromatogram). The substrates generally, but not always, consist of a moiety, which can be recognized by the enzyme and thereby confer specificity of the substrate, and another moiety enabling signal generation. The signal can be a chromogenic, fluorogenic, chemiluminescent or other measurable signal. Upon interaction with an enzyme, the substrate is normally cleaved by the enzyme, thereby resulting in changes in colorimetric, fluorescent or chemiluminescent signal, which can be detected using an appropriate instrument. Appropriate concentrations of the substrate in the reagent mixes can be optimized empirically. Both reagent mixes may contain the enzyme inhibitor, albeit at different concentrations, so long as the inhibitor concentrations in the two reagent mixes are distinct and enable signal ratio distinction between inhibitor resistant and susceptible enzymes.

In certain embodiments, a chemiluminescent substrate is used in the assay as chemiluminescent substrates generally result in wider linear range. Appropriate chemiluminescent substrates include, but are not limited to, dioxetane derivatives and luciferin derivatives.

When the chemiluminescent substrate is a dioxetane derivative, the dioxetane moiety is released from the substrate upon interaction with the enzyme in the sample. Light production from released dioxetane is normally enabled by elevating the reaction pH to alkaline pH, e.g., pH 11. If the optimal pH for the enzyme to be tested in the sample is significantly below the alkaline pH, it is necessary to perform the assay in a two-step fashion, where the enzymatic reaction is first performed at lower pH to cleave the substrate, followed by elevation of the pH to alkaline pH to trigger light production.

When the chemiluminescent substrate is a luciferin derivative, the luciferin moiety is released from the substrate upon interaction with the enzyme in the sample. Light production is enabled by luciferase, which oxidizes luciferin to oxyluciferin to cause light production. If the optimal pH of the enzyme is nearly the neutral pH, a one-step is feasible since luciferase can function efficiently at neutral pH. In a one-step assay, the enzymatic reaction and subsequent signal production and detection occur simultaneously, which simplifies the assay procedure and generally reduces assay variability. Examples 1 and 2 provide compositions of the reagent mixes of an assay, which uses 4, 7-dimethyl N-acetylneuraminic acid-O-luciferin as the substrate for detection of influenza viral enzymatic activity and inhibition by oseltamivir carboxylate.

The substrate may not always enable changes in signal intensity upon interaction with the specific enzyme. Instead, it may cause other changes in signal, e.g., signal patterns. For example, a protease substrate is a peptide or modified peptide, which can be cleaved by the protease. Cleavage of the peptide substrate results in two smaller fragments, which may have similar signal intensity to the uncleaved substrate. However, the cleaved fragments can be detected with a separation and detection device such as an HPLC or with a non-separation device such as a mass spectrometer. An example is provided in Example 4.

In certain embodiments, one of the reagent mixes contains no enzyme inhibitor while the other reagent mix contains an enzyme inhibitor at an appropriate concentration. The inhibitor concentration may be determined empirically by testing a sufficient number of samples, some of them containing inhibitor-resistant enzyme while other containing inhibitor-susceptible enzyme. An appropriate inhibitor concentration should result in significantly different signal ratios of the two reactions between the inhibitor-resistant and inhibitor-susceptible enzymes. It is understood that the reagent mix containing no enzyme inhibitor may still contain an amount of enzyme inhibitor so long as the inhibitor concentrations in the two reagent mixes are distinct and enable signal ratio distinction between inhibitor resistant and susceptible enzymes.

The reagent mixes can be formulated as concentrated solutions, e.g., 2× concentrated solutions. An equal volume of the sample in a sample buffer is mixed with the 2× concentrated reagent mixes to initiate the reaction when 2× concentrated reagent mixes are used. The reagents in the reagent mixes can also be lyophilized to remove the water, in which case full mounts of sample in 1× solution can be added to the reagent mixes to initiate the reactions.

The signal intensity of the two reactions is measured with an appropriate instrument: a photometric device can be used to measure chromogenic signal, a fluorometer can be used to measure fluorogenic signal, and a luminometer can be used chemiluminescent signal. The signal ratio of the two reactions can be computed and used to indicate the degree of resistance of the enzyme to its inhibitor. The signal ratio can be expressed in several forms. For example, it can be expressed as the signal ratio of Reaction I to Reaction II or as that of Reaction II to Reaction I or as the multiple of such a ratio, e.g., 10× (Reaction II signal÷Reaction I signal).

The cutoff ratio for resistance of an enzyme to an inhibitor can be determined by testing a large number of samples that include both resistant and susceptible samples by correlating the signal ratios to clinical outcomes or gold standard test results such as $IC_{50}$ values and sequencing based detection for mutations.

The signal in the two reactions can be measured sequentially using a single-tube signal measurement device. The signals for the two reactions are recorded and used to compute the signal ratio, which is indicative of inhibitor resistance. Use of this device is thus somewhat cumbersome. Alternatively, the two reactions can be conducted using a microwell plate, where the signal can be simultaneously measured using a microwell plate reader. However, microwell plate readers are not designed for this type of assay, which comprises only two reactions, and are generally not portable.

In the present invention, a device with dual signal measurement capability is provided. The device comprises two detection chambers and allows that both reaction tubes can be placed in the detection chambers at the same time. The device has one or two sensors for detection of the signal. Appropriate signal detection sensors are those that can provide sufficient sensitivity. They include, but are not limited to, photomultiplier tube (PMT) and photodiodes for detection of light signal.

In certain embodiments, the device has two signal detection sensors, one for each detection chamber. The use of two signal detection sensors such as photodiodes has several advantages. First, the device needs no moving part, which considerably reduces the manufacturing cost and size of the instrument, as each detection chamber has its own signal detection sensor. Second, the signals from the two reactions placed in the two sample chambers can be detected simultaneously rather than sequentially. Third, the assay procedure is simplified as the signal ratio can be computed and test result interpreted automatically by the device. Thus, the use of a device with two detection chambers further simplifies the procedure for detection of enzyme inhibitor resistance. In other embodiments, the device comprises multiples of two detection chambers, e.g., 4 detection chambers, to accommodate simultaneous detection of more than one sample.

For many enzymes that are important therapeutic targets, two or more inhibitors have been developed for pharmacological intervention. Examples include, but are not limited to, influenza viral neuraminidase, HIV protease, and bacterial beta lactamase. At present, beta lactamase inhibitors include clavulanic acid, sulbactam, and avibactam in addition to many lactam antibiotics such as carbapenems, which are antibiotics that are resistant to degradation of susceptible beta lactamases. In certain embodiments, an assay that can detect resistance to two or more enzyme inhibitors is preferred. This type of assays consists of one reagent mix, which contains no inhibitor, and several versions of reagent mixes, each of which contains a distinct enzyme inhibitor. A sample testing can be carried out by adding the sample to the reagent mix without inhibitor and all variations of reagent mixes each of which contains a distinct inhibitor. Signal ratio can be calculated for each enzyme inhibitor.

The signal of the reagent mix without an inhibitor can be used to determine whether the enzyme is present in the sample. The cutoff value may be determined by testing an appropriate number of appropriate samples. For example, the cutoff value may be set at 3 standard deviations above the mean for 1000 negative samples and verified by testing 100 positive samples. Likewise, the cutoff value for signal ratio of Reagent Mix II to Reagent Mix I may be determined for each enzyme and each of its inhibitors by testing an appropriate number of appropriate samples. It is understood that there may be a minimum of enzyme concentration for valid determination of its resistance to an inhibitor, which may be determined by testing an appropriate number of appropriate positive samples.

EXAMPLES

The following examples are provided by way of illustration only by means of various particular embodiments and are in no way exhaustive or exclusive.

Example 1: Detection of Influenza Viral Resistance to Oseltamivir Carboxylate

This example illustrates how the method described in the present invention can be used to differentiate an oseltamivir carboxylate susceptible influenza virus from a resistant virus. Oseltamivir carboxylate is the active form of the key ingredient in TAMIFLU™.

The enzyme to be tested is the influenza viral neuraminidase, which is the target of several inhibitors, one of which is oseltamivir carboxylate. The chemiluminescent substrate used for detection of influenza viral neuraminidase is a luciferin derivative, i.e., 4, 7-dimethyl N-acetylneuraminic acid-O-luciferin. In the presence of influenza virus or its neuraminidase in the sample, the luciferin moiety of the substrate is released by the enzyme. In the presence of luciferase, luciferin is then oxidized to oxyluciferin to produce light signal. Since both influenza viral neuraminidase and luciferase can function at neutral pH, luciferase can be added to the enzymatic reaction mixes to create a one-step assay.

The two reagent mixes, Reagent Mix I and Reagent Mix II, were prepared as follows: Composition of Reagent Mix I:

| Imidazole | 50 mM adjust the pH to 7.0 to 7.2 |
|---|---|
| BSA | 0.1% |
| ATP-Na | 4 mM |
| DTT | 10 mM |
| Coenzyme A | 1 mM |
| MgCl2 | 15 mM |
| CaCl2 | 4 mM |
| Gentamycin | 2.5 mg/100 mL |
| Substrate | 10 µg/mL |
| Luciferase | 2 mg/100 mL |
| Mannitol | 4% |
| Sucrose | 1% |

The composition of Reagent Mix II was the same as Reagent Mix I except that it also contained 50 nM of oseltamivir carboxylate. It is understood that other concentrations of the inhibitor may be used in the assay. 0.25 mL of Reagent Mixes was aliquoted in 75×12 mm glass vials. The reagent mix aliquots were then lyophilized to remove the moisture in the reagent mixes.

To perform detection, cultured influenza virus was diluted in 10 mM HEPES buffer (pH 7.4) at 1:100 and 1:1000 dilutions. Two strains of influenza virus were used in this example: A/Georgia/17/2006, which is a wild type virus that is susceptible to Tamiflu, and A/Georgia/20/2006, which is a mutant that is resistant to Tamiflu. 0.25 mL sample of each dilution for each virus strain was added to both Reagent Mixes I and II. After incubation at room temperature for 5 minutes, the light signal in the reactions was measured using a Luminometer. The signal was measured in terms of relative light units (RLU) and used to calculate the signal ratio.

The signal ratio of the two reactions was computed as follows:

$$\text{Signal Ratio (R-Factor)} = 10 \times (\text{Reagent Mix II Signal} \div \text{Reagent Mix I Signal})$$

The signal ratio computed according to the above formulae is defined as the R-Factor. As shown in Table 1, the average R-Factor values for the oseltamivir carboxylate (OC) susceptible influenza virus were 0.27 and 0.32 for 1:100 and 1:1000 dilutions, respectively. In contrast, the average R-Factor values for the oseltamivir carboxylate (OC) resistant mutant influenza virus were 7.14 and 5.26 for 1:100 and 1:1000 dilutions, respectively. The signal ratios for the OC resistant and susceptible influenza virus were clearly distinguishable. Therefore, the two-reaction method described in the present invention can be used to differentiate the OC resistant influenza virus from the susceptible virus.

TABLE 1

Determination of OC Resistance Status Using Two Reactions Format

| Virus | OC Resistance Phenotype | Sample Dilution | Rep 1 | Rep 2 | Rep 3 | Mean | SD | CV (%) |
|---|---|---|---|---|---|---|---|---|
| A/Georgia/17/2006 (WT) | Susceptible | 1:100 | 0.28 | 0.27 | 0.26 | 0.27 | 1.85 | 4.9 |
|  |  | 1:1000 | 0.30 | 0.35 | 0.30 | 0.32 | 2.49 | 7.8 |
| A/Georgia/20/2006 (H274Y) | Resistance | 1:100 | 7.14 | 7.69 | 7.14 | 7.14 | 0.05 | 4.2 |
|  |  | 1:1000 | 4.76 | 5.56 | 5.26 | 5.26 | 0.15 | 7.9 |

Example 2: Correlation Between Signal Ratios and Level of Inhibitor Resistant Influenza Virus This example examined the relationship of the degree of drug resistance of influenza virus in a sample to an influenza viral neuraminidase inhibitor oseltamivir carboxylate (OC) and the signal ratios or the R-Factor values. Reagent Mixes I and II were prepared according to the formulations described in Example 1. In order to produce samples with variable degrees of OC resistance, an OC susceptible virus (A/H1N1p/CA/07/2009) was mixed with an increasing amount of OC resistant virus (A/H1N1p/NC/39/2009). The composite samples were then tested with Reagent Mixes I and II as described in Example 1. A device with two detection chambers, each of which had its own photodiode sensor, was used to measure the signal intensity of the two reactions.

Figure 1:
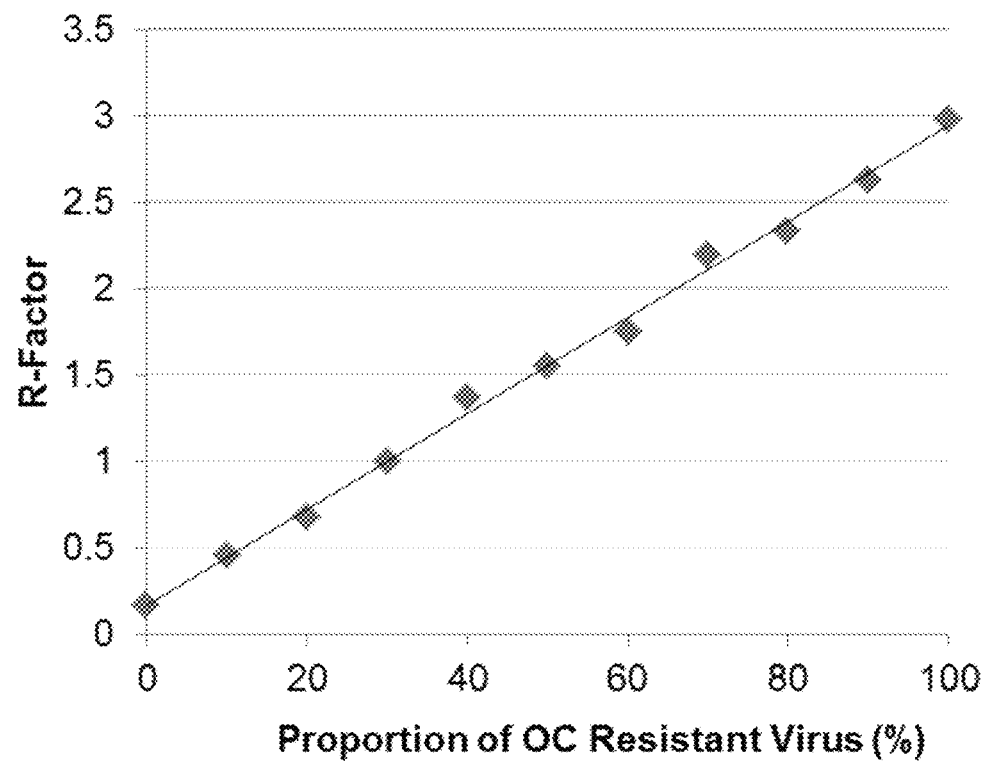

The signal ratios were expressed as R-Factor values as described in Example 1. The R-Factor values increased as the proportion of the OC resistant virus increased in the samples with a correlation coefficient of 0.9964 (FIG. 1), indicating that the R-Factor value is indicative of the degree of oseltamivir resistance.

Example 3: Utility of Signal Ratios for Detection of Influenza Virus Resistant to a Neuraminidase Inhibitor Reagent Mixes I and II with compositions substantially similar to those described in Example 1 were used in the experiments in the current example.

Current method of choice for determination of drug resistance of an influenza virus is the $IC_{50}$ determination method. However, determination of $IC_{50}$ involves testing a sample using 8-12 reactions. The method described in this invention uses only two reactions. This example showed that like the $IC_{50}$ values, the R-Factor values obtained using the methods and reagents described in this invention can differentiate the drug resistant influenza virus from the susceptible virus.

A total of 202 influenza clinical isolates were used in the study in this example. These isolates consist of both OC resistant and susceptible viruses, including 104 H1N1 virus isolated from the 2008/2009 influenza season (08/09 H1N1 seasonal flu virus), 9 H1N1 virus isolated from the 2007/2008 influenza season (07/08 H1N1 season flu virus), 35 H3N2 virus isolated from 2008/2009 influenza season (08/09 H3N2 seasonal flu virus), and 54 Type B influenza virus isolated from recent years. All these virus isolates were collected in the United States. It is known that nearly all of 08/09 seasonal N1N1 virus circulating in U.S. carried the H274Y mutation in the neuraminidase gene, which confers resistance to oseltamivir carboxylate. All other virus isolates, including 07/08 H1N1, 08/09 H3N2 and Type B isolates, were expected to be susceptible to OC.

The $IC_{50}$ value for each of the 202 clinical isolates was determined essentially according to a published article (Antimicrobial Agent and Chemotherapy. Vol. 57, Pages 5209-5215). The $IC_{50}$ profiles for these virus isolates are summarized in Table 2. As expected, the 08/09 H1N1 isolates showed high degree of resistance to OC with $IC_{50}$ values ranging from 79.58 to 717.97 nM. In contrast, the $IC_{50}$ values for 07/08 H1N1 and 08/09 H3N2 isolates were considerably lower, ranging from 0.40 to 7.10 nM, indicating that these viruses were highly susceptible to OC. Type B virus has been known to have reduced susceptibility to OC, which is consistent with the $IC_{50}$ values for this group Type B virus. The mean $IC_{50}$ value for Type B virus was 18.69 nM, ranging from 5.46 to 36.24 nM. In general, there were two distinct groups, one with high $IC_{50}$ values (>79 nM) and one with low $IC_{50}$ value (<37 nM). Nonetheless, OC may still be effective in treating infections of Type B influenza virus.

If the OC resistance cutoff value of $IC_{50}$ is set at 50 nM, then 100% of the 80/09 H1N1 virus isolates are resistant to OC while 100% of 07/08 H1N1, 08/09 H3N2 and Type B virus isolates are susceptible to OC.

TABLE 2

Oseltamivir Carboxylate $IC_{50}$ Profiles

| | | Expected OC Resistance Phenotype | | | |
|---|---|---|---|---|---|
| | | Resistant | Susceptible | | |
| | | Flu Virus Strain | | | |
| | | 08/09 A/H1N1 | 07/08 A/H1N1 | 08/09 A/H3N2 | Type B |
| $IC_{50}$ (nM) | N | 104 | 9 | 35 | 54 |
| | Mean | 244.71 | 2.64 | 1.55 | 18.69 |
| | SD | 133.25 | 1.86 | 1.10 | 6.45 |
| | Range | 79.58-717.97 | 1.80-7.26 | 0.40-7.10 | 5.46-36.24 |
| % Susceptible | | 0 | 100 | 100 | 100 |
| % Resistant | | 100 | 0 | 0 | 0 |

These isolates were also tested using the two reaction method and a detection device with dual detection chambers. Reagent Mixes I and II were prepared essentially according to the compositions described in Example 1. The signal detection device contained dual detection chambers, each of which had a photodiode sensor so that the two reactions in reaction tubes could be placed into the device at the same time and signals from both reactions could be measured simultaneously.

Diluted samples were added to Reagent Mixes I and II to initiate the reactions. After incubation at room temperature for approximately 15 minutes, the signals in the two reactions were measured. The R-Factor values were computed using the Excel software and summarized in Table 3. Like the $IC_{50}$ values, the R-Factor values can also be separated into two distinct groups, the high and low R-Factor value groups. As expected, the high R-Factor group consists of only the 08/09 H1N1 virus whereas the lower R-Factor group consists of 07/08 H1N1 virus, 08/09 H3N2 virus and Type B virus.

TABLE 3

Detection of OC Resistance Using the Two Reaction Format

| | | Expected OC Resistance Phenotype | | |
|---|---|---|---|---|
| | | Resistant Virus | Susceptible Virus Strain | |
| | | 08/09 A/H1N1 | 07/08 A/H1N1 | 08/09 A/H3N2 | Type B |
| R-Factor Value | N | 104 | 9 | 35 | 54 |
| | Mean | 4.29 | 0.23 | 0.31 | 0.74 |
| | SD | 0.39 | 0.11 | 0.30 | 0.24 |
| | Range | 3.75-6.02 | 0.05-0.38 | 0.83-1.29 | 0.42-1.67 |

If a cutoff R-Factor value is set at 2.40, all 08/09 H1N1 virus isolates are resistant to OC while all of 07/08 H1N1, 08/09 H3N2 and Type B virus isolates are susceptible to OC. The test results using the two reaction method described in this invention is in 100% agreement with the $IC_{50}$ assay results when the $IC_{50}$ cutoff value is set at 50 nM (Table 4). Thus, the two reaction method as described in this invention can be used to determine OC resistance of influenza virus.

TABLE 4

Detection of Oseltamivir Susceptibility with QFlu Combo Test

| | | Determined by $IC_{50}$ Method | | |
|---|---|---|---|---|
| | | Resistant | Susceptible | Total |
| Determined by Two-Reaction Method | Resistant | 104 | 0 | 104 |
| | Susceptible | 0 | 98 | 98 |
| | Subtotal | 104 | 98 | 202 |
| % Agreement | | 100% | 100% | |

When the R-Factor values are plotted against the $IC_{50}$ values, it shows two well separated groups of influenza virus isolates: the high $IC_{50}$ and high R-Factor value group and the low $IC_{50}$ and low R-Factor value group (FIG. 2). These results show that the test results from the two reaction format as well as the device with two test tube chambers can be used to detect drug resistance of influenza virus.

It is understood that the two reaction method can be modified by those skilled in the art for detection of resistance of any enzyme to its inhibitor other than the influenza viral neuraminidase described in Examples 1-3.

Example 4: Detection of Resistance of HIV Protease to its Inhibitors

Proteases are enzymes that cleave or digest proteins. They are often specific for an amino acid sequence. HIV-1 protease cleaves the tyrosine-proline peptide linkage. Thus, the substrate of HIV-1 protease can be a peptide containing the cleavage site Tyr-Pro. A suitable substrate is a peptide consisting of the amino acid sequence Fluorescein-Glu-Ser-Gln-Asn-Tyr-Pro-Ile-Val-Gln-Lys, where fluorescein is a fluorophore. Cleavage of the substrate by HIV-1 protease results in two smaller peptides Fluorescein-Glu-Ser-Gln-Asn-Tyr and Pro-Ile-Val-Gln-Lys, which can be separated and detected on an HPLC.

The 2× Reagent Mix I solution for the HIV Protease Assay can be prepared as follows: 4 micromole/L substrate, 0.2 M sodium acetate, 2.0 M sodium chloride, 2.0 mM ethylenediaminetetraacetic acid (EDTA), 2.0 mM dithiothreitol (DTT), 20% dimethyl sulfoxide (DMSO), 2 mg/mL bovine serum albumin (BSA), pH 5. The 2× Reagent Mix II is the same as Reagent Mix I except for an additional HIV protease inhibitor such as Nelfinavir at, for example, 100 nM. Reactions are carried out by mixing 0.1 mL 2× Reagent Mix with an equal volume of sample in an appropriate sample buffer (e.g., 10 mM Acetate, pH 5, 0.1% BSA, and 0.5% Triton X-100). After incubation at 37° C. for 15 minutes, the reactions are stopped by mixing with 0.1 mL of 10 mM NaOH. The resulting reaction solutions are then analyzed with an HPLC using a C18 column and a fluorescent detection system. There should be two fluorescent peaks, one for the product and one for the uncleaved substrate (less hydrophobic). The product peak areas—the signal intensities—of the two reaction solutions are computed and used to determined resistance of the HIV protease in the sample to the inhibitor.

Controls may be carried out in parallel. For example, one positive control contains an HW protease resistant to the inhibitor while another control contains an HIV protease inhibitor to establish the boundary of the signal ratios between susceptible and resistant HIV proteases. The signal ratio cutoff value may be established by testing a large number of samples with known inhibitor resistance status.

Example 5: Simultaneous Detection of Influenza Viral Neuraminidase Resistance to Oseltamivir Carboxylate and Zanamivir This example illustrates how resistance to two inhibitors, oseltamivir carboxylate and zanamivir, of influenza viral neuraminidase can be performed simultaneously. The assay reagents consist of Reagent Mix I, which contained no inhibitor, Reagent Mix IIa, which contains the inhibitor oseltamivir carboxylate at 50 nM, and Reagent Mix IIb, which contains zanamivir at 50 nM.

Reagent Mix I and Reagent Mix IIa can be prepared as described in Example 1. The composition of Reagent Mix IIb is the same as Reagent Mix IIa except that 50 nM of oseltamivir carboxylate is replaced with 50 nM of zanamivir. A sample testing is carried by adding the sample with appropriate dilution and sample buffer to Reagent Mixes I, IIa and IIb to initiate the reactions. The signal is measured for all corresponding Reactions I, IIa and IIb. Signal ratios are computed for zanamivir and oseltamivir for each sample and can be expressed as R-Factor values as described in Example 1. R-Factor cutoff values for zanamivir and oseltamivir carboxylate can be based on comparison with the $IC_{50}$ data.

Example 6: Detection of Beta Lactamase Activity

Antibiotics containing the characteristic beta lactam ring are the mainstay of pharmaceuticals for treating bacterial infections. They include both penicillin and cephalosporin-types of antibiotics. However, a great number of bacterial species develop resistance to the beta lactam antibiotics by acquiring the ability to produce beta lactamase, which can degrade the beta lactam antibiotics. In this example, only one reagent mix was used for detection of beta lactamase activity in a sample. Presence of beta lactamase activity in a sample indicates resistance of the bacterial species to beta lactam antibiotics.

The reagent mix was prepared as a 2× concentrated solution. The 2× concentrated reagent mix contained 50 mM HEPES (pH 7.0 to 7.2), 0.2 mM $ZnCl_2$, 8 mM ATP, 10 mM DTT, 0.1 mM Coenzyme A, 5 micrograms/mL luciferase, 0.01 mM Cephalosporin-O-Luciferin, 0.1 mg/mL BSA, 8 mM $CaCl_2$, 30 mM $MgCl_2$, and 1% Triton X-100. Cephalosporin-O-Luciferin was used as a beta lactamase substrate. This substrate was synthesized and purified according to a procedure published in a scientific article (Angew. Chem. Int. Ed. 2007 Vol. 46, pp. 7031-7034), which is cited here solely as a reference.

Figure 3:
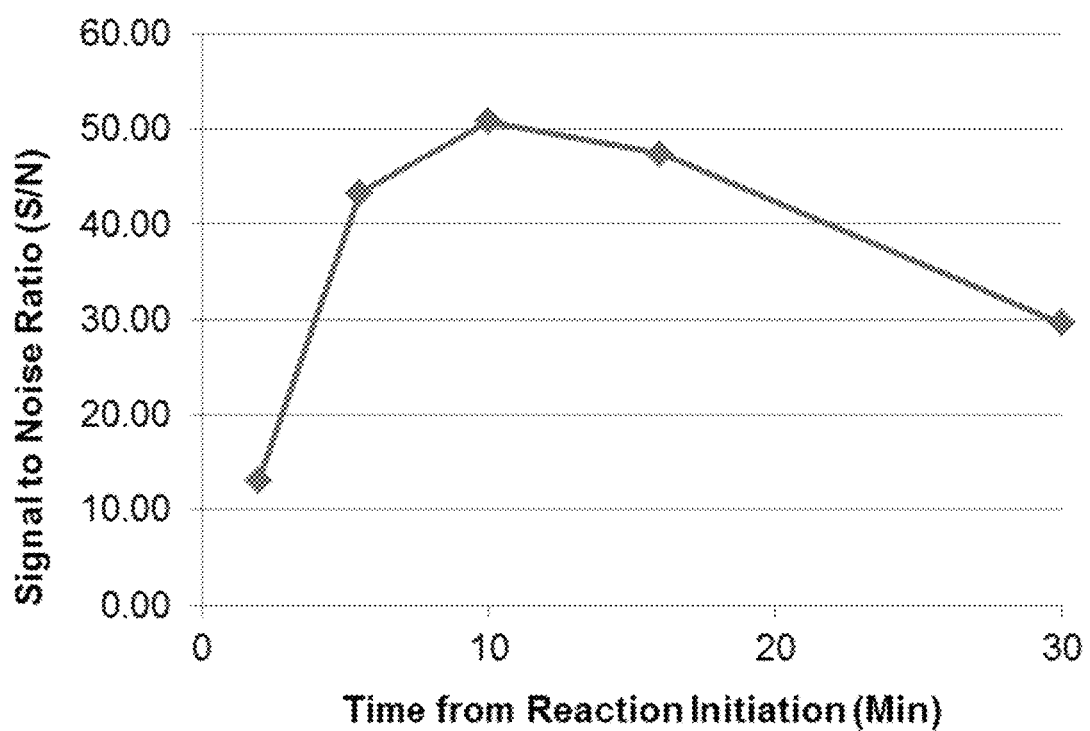
Figure 4:
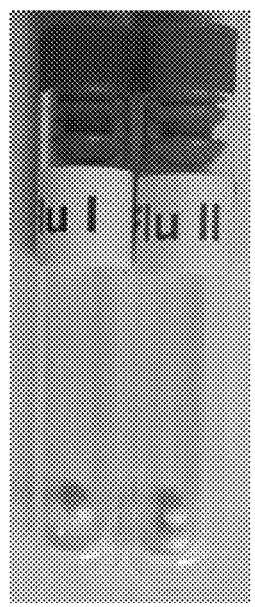

The assay was performed by diluting 50 microliters of the 2× concentrated reagent mix with 47.5 microliters of deionized water. The reaction was initiated by adding 2.5 microliters of a lysate of E. coli cells, which was induced to express a recombinant beta lactamase (HSV-2). Signal to noise ratios of greater than 10 were observed within 2 minutes after the reaction was initiated (FIG. 3). The signal to noise ratio peaked at around 10 minutes. Decrease in signal after 10 minutes might indicate depletion of the substrate in the reaction. Nonetheless, the signal to noise ratios remained well above 1.0 throughout the reaction period of 30 minutes (FIG. 3).

Example 7: Detection of Resistance to a Beta Lactamase Inhibitor and an Antibiotic In this example, the assay according to the present invention can simultaneously detect resistance of a beta lactamase to a beta lactamase inhibitor (clavulanate) and imipenem, which is a carbapenem-type of antibiotic. Five species of beta lactamase were tested in this example. These five beta lactamase species are a New Deli Metallo-beta lactamase (NDM-2), p99, SHV-2, KPC-2 and TEM-2. The characteristics of these beta lactamases are summarized in Table 5.

TABLE 5

Characteristics of Beta Lactamases Used in Studies in Example 7*

| BLM Name | Bush-Jacoby (2009) | Defining Characteristics* | Inhibited by |
| --- | --- | --- | --- |
| p99 | 1 | Greater hydrolysis of cephalosporins than benzylpenicillins; hydrolyze cephamycins | Carbapenems |
| SHV-2 | 2 | Increased hydrolysis of oxyimino-beta lactams (extended spectrum beta lactams) | Clavulanate, tazobactam, |
| TEM-2 | 2 | Similar hydrolysis of benzylpenicillins and cephalosporins | Clavulanate, tazobactam, carbapenems |
| KPC-2 | 2 | Increased hydrolysis of carbapenems, oxyimino-beta lactams, and cephamycins | Not by EDTA |
| NDM-2 | 3 | Preferential hydrolysis of carbapenems | EDTA |

*Adapted from Bush and Jacoby, Updated Functional Classification of Beta Lactamases. Antimicrobial Agents and Chemotherapy. 54: 969-976 (2010).

Genes encoding five species of beta lactamase were synthesized and cloned into an E. coli expression vector. The E. coli cells transformed with the expression vector containing the gene encoding a beta lactamase was induced to express the enzyme. The cells were then pelleted, suspended in a sample buffer (Fisher Scientific Cat. No. 90084) and sonicated to lyse the cells.

2× concentrated reagent mixes were prepared. The 2× reagent mix without a beta lactamase inhibitor or antibiotic (Reagent Mix I) was prepared according to the composition provided in Example 6. The 2× concentrated reagent mix containing a beta lactamase inhibitor or imipenem (Reagent Mix IIb) was prepared by supplementing the Reagent Mix I with 64 micrograms/mL of clavulanate (Reagent Mix IIa) or 64 micrograms/mL of imipenem (Reagent Mix IIb).

Reactions were carried out by diluting 50 microliters of 2× reagent mixes into 45 microliters of deionized water, followed by addition of 5 microliters of cell lysate. Reactions without cell lysate were used as the negative controls since studies had shown that cell lysates of E. coli cells without expressing a beta lactamase had similar signal to the reactions without cell lysate. Light signal was measured using a luminometer after 15 min incubation at room temperature. The signal in Reagent Mix I was used to detect the presence of beta lactamase in the sample by comparing the signal in the reaction to that of negative controls while the signal ratio was used to determine the resistance of the beta lactamase to clavulanate or imipenem.

In this example, the signal ratios were expressed as R-Factor values, which were calculated as follows:

R-Factor=10×(Reagent Mix II Signal÷Reagent Mix I Signal)

The higher the R-Factor is, the more resistant it is to the beta lactamase inhibitor or antibiotics present in Reagent Mix II. As shown in Table 6, the test results are consistent with the expected resistance profiles for each beta lactamase tested. For example, the R-Factor value of SHV-2 and TEM-2 for clavulanate was 0.23 and 1.18 respectively, indicating that both of these beta lactamases are susceptible to clavulanate. A combination antibiotic drug, which contains a beta lactam antibiotic and clavulanate such as Augmentin, would be effective in treating an infection of a bacterial species even expressing SHV-2 and/or TEM-2 type of beta lactamase.

TABLE 6

Test Results from Experiments Described in Example 7

| Sample | BL Name Test Dilution | p99 1:200 | SHV-2 1:10 | TEM-2 Undiluted | KPC-2 1:10 | NDM-2 1:2 |
| --- | --- | --- | --- | --- | --- | --- |
| Reagent Mix I | S/N | 47.63 | 44.04 | 42.42 | 44.76 | 21.60 |
| Reagent Mix IIa | S/N | 48.00 | 1.00 | 5.00 | 40.00 | 13.00 |
| (Clavulanate) | R-Factor | 10.08 | 0.23 | 1.18 | 8.94 | 6.02 |
| Reagent Mix IIb | S/N | 1.01 | 11.00 | 24.00 | 43.00 | 13.00 |
| (Imipenem) | R-Factor | 0.21 | 2.50 | 5.66 | 9.61 | 6.02 |

BL    Beta Lactamase
S/N    Signal to Noise Ratio

Conversely, Augmentin would not have been effective in treating an infection of a bacterial species expressing p99, KPC-2 and/or NDM-2, which had high R-Factor values for clavulanate. Meanwhile, TEM-2, KPC-2 and NDM-2 showed strong resistance to imipenem, a type of carbapenems, whereas SHV-2 showed modest resistance while p99 showed no resistance to imipenem. This information would be highly useful for guiding an antibiotic prescription.

Example 8: An Assay for Detection of Carbapenemase-Producing Organisms

Since its discovery and first clinical use in 1940's, beta lactam antibiotics have saved countless lives. However, widespread use of these antibiotics led to widespread resistance of bacterial species to these antibiotics, many due to the appearance of beta lactamases. One class of beta lactams, the carbapenems, is resistant to beta lactamases and has been preserved as the antibiotics of "last-resort". However, beta lactamases which can degrade carbapenems and are commonly referred to as carbapenemases have appeared. Organisms carrying a carbapenemase (carbapenemase-producing organisms, CPO) have increased dramatically in recent years. In some parts of the world such as the East Coast of the United States, CPO's are considered endemic. This is alarming because infection with a CPO may lead to high mortality and morbidity rate. A rapid assay for CPO is desirable for use in diagnosis and surveillance.

Since carbapenems inhibit beta lactamases except for a carbapenemase, an assay for detection of a CPO can be formulated according to the present invention. The CPO assay comprises two reagents, which can be formulated as described in Example 7. Reagent Mix I comprises a master mix for detection of beta lactamase activity whereas Reagent Mix II comprises a master mix containing a carbapenem. The signal from Reagent Mix I indicates the presence or absence of beta lactamase activity in the sample while the signal ratio of the two reagents, e.g., an R-Factor value as described in Example 7, indicates whether the beta lactamase is a carbapenemase. A sample containing carbapenemase activity as indicated by above cutoff signal from Reagent Mix I and high R-Factor value is a sample containing a CPO.

The cutoff R-Factor value may be determined by testing an appropriate number of appropriate samples containing carbapenemase activity or non-carbapenemase beta lactamase activity as determined by a gold standard, e.g., a method (M100-S22) by Clinical and Laboratory Standards Institute (CLSI).

Example 9: Determination of Resistance to a Beta Lactamase Inhibitor Using a Single Bacterial Colony in a Culture Current clinical practice for determination of antibiotic resistance normally involves two sequential overnight cultures. The first culture confirms that there is an infection in a patient. When the first culture is on an agar plate, the cultured bacterial species grow as individual colonies. A single colony is normally suspended in a solution, plated on an agar plate and subjected to antibiotic susceptibility detection commonly using a filter disc containing an antibiotic. Alternatively, when a clinical sample is cultured in a liquid medium as in a blood culture, the first culture (if positive) can also be used for antibiotic susceptibility testing using a second culture. These methods take too long for it to be effective in guiding therapeutic decisions.

The methods disclosed in the present invention can be used to determine whether a bacterial colony produces a beta lactamase and, if yes, whether the beta lactamase is resistant to a beta lactamase inhibitor such as clavulanate and carbapenems. Clavulanate is used in a formulation of certain antibiotics such as AUGMENTIN, which contains both clavulanate and amoxicillin. As described in EXAMPLE 7, the assay consisted of two reagents, Reagent Mix I and Reagent Mix II, where Reagent Mix I contained one master mix without clavulanate while Reagent Mix II contained a master mix with clavulanate. In this example, reagent mixes equivalent to 0.25 mL of the master mixes were lyophilized in test tubes.

Patient samples were cultured overnight on an agar plate. A single colony was suspended in 2.5 mL sample buffer as described in EXAMPLE 7, of which 0.25 mL was added to Reagent Mixes I and II vials. After incubation at room temperature for 15 min, the reagent vials were inserted into a luminometer for signal measurement. As shown in Table 7, of the 23 patient samples tested, 13 (56.5%) clearly showed beta-lactamase (BL) activity with signal to noise ratio (S/CO) greater than 1.0, a high prevalence rate reflecting widespread use of beta-lactam antibiotics in the region. Of the 13 BL positive samples, 8 (61.5%) showed low R-Factor value, indicating that the beta-lactamases in these samples were susceptible to clavulanate. There were five BL positive samples showing high R-Factor values, indicating that the beta-lactamases in these bacterial species were resistant to clavulanate. These results showed that the assay was sensitive and could be used for detection of bacterial resistance to a beta lactamase inhibitor using a single cultured bacterial colony.

The test results can be used to guide decisions on antibiotic prescription: for those patients infected with a bacterial species without beta lactamase activity, treatment with an older version of beta lactam antibiotic such as amoxicillin should be effective; for those patients infected with a bacterial species with a beta lactamase that is susceptible to clavulanate, treatment with a combination antibiotic containing an antibiotic and clavulanate such as AUGMENTIN should be effective; for those patients infected with a bacterial species with beta lactamase that is resistant to clavulanate, a more recent antibiotics, a carbapenem or non-lactam antibiotic should be used.

TABLE 7

Determination of Clavulanate Resistance Using a Single Bacterial Colony

| No. | Sample ID | Bacterial Sp. | Reagent I Signal (S/CO)* | R-Factor** | Interpretation |
|---|---|---|---|---|---|
| 1 | 1845 | Klebsiella pneumoniae | 12.36 | 0.07 | Positive for BL; susceptible to CA |
| 2 | 1847 | Klebsiella pneumoniae | 11.44 | 0.15 | Positive for BL; susceptible to CA |
| 3 | 1820 | Pseudomonas aeruginosa | 1.68 | 3.67 | Positive for BL; resistant to CA |
| 4 | 1765 | Acinetobacter baumannii | 0.44 | N/A*** | Negative for BL |
| 5 | B612 | E coli | 30.44 | 0.27 | Positive for BL; susceptible to CA |
| 6 | B616 | E coli | 22.16 | 0.13 | Positive for BL; susceptible to CA |
| 7 | 1789 | Pseudomonas aeruginosa | 21.82 | 1.14 | Positive for BL; susceptible to CA |
| 8 | 1800 | Pseudomonas aeruginosa | 13.05 | 11.13 | Positive for BL; resistant to CA |
| 9 | B654 | Pseudomonas aeruginosa | 0.54 | N/A | Negative for BL |
| 10 | 2046 | Klebsiella pneumoniae | 0.15 | N/A | Negative for BL |
| 11 | 2065 | Acinetobacter baumannii | 0.19 | N/A | Negative for BL |
| 12 | 1974 | Acinetobacter baumannii | 0.15 | N/A | Negative for BL |
| 13 | 1962-2 | Pseudomonas aeruginosa | 7.05 | 15.47 | Positive for BL; resistant to CA |
| 14 | 1963 | Pseudomonas aeruginosa | 3.22 | 19.95 | Positive for BL; resistant to CA |
| 15 | B678 | E coli | 0.96 | N/A | Negative for BL |
| 16 | 2017 | Acinetobacter baumannii | 0.26 | N/A | Negative for BL |
| 17 | 2015 | Acinetobacter baumannii | 9.65 | 1.74 | Positive for BL; susceptible to CA |

TABLE 7-continued

Determination of Clavulanate Resistance
Using a Single Bacterial Colony

| Sample No. | ID | Bacterial Sp. | Reagent I Signal (S/CO)* | R-Factor** | Interpretation |
|---|---|---|---|---|---|
| 18 | 2022-1 | Acinetobacter baumannii | 1.47 | 1.31 | Positive for BL; susceptible to CA |
| 19 | 1959 | Klebsiella pneumoniae | 0.10 | N/A | Negative for BL |
| 20 | B650 | Klebsiella pneumoniae | 10.52 | 0.11 | Positive for BL; susceptible to CA |
| 21 | B671 | Klebsiella pneumoniae | 5.53 | 4.12 | Positive for BL; resistant to CA |
| 22 | 1962-1 | Klebsiella pneumoniae | 0.56 | N/A | Negative for BL |
| 23 | 1978 | Acinetobacter baumannii | 0.89 | N/A | Negative for BL |

*BL (β-lactamase) positive cutoff RLU: 375:;

**CA (clavulanate) resistance cutoff R-Factor value: 2.50

***N/A: R-Factor value is not applicable due to absence of beta lactamase activity as determined with Reagent Mix I.

Example 10: Determination of Resistance to a Beta Lactamase Inhibitor Using a Liquid Bacterial Culture In this example, a liquid bacterial culture is used for detection of beta lactamase activity and its resistance to a beta lactamase inhibitor. Although there may be more than one bacterial species in a liquid bacterial culture of a clinical specimen, detection of beta lactamase and its resistance to an inhibitor in certain liquid bacterial culture such as a blood culture is still highly useful. A positive bacterial liquid culture can be diluted in a sample buffer at an appropriate dilution, which can be experimentally determined. Examples of dilutions include, but are not limited to, 1:1, 1:2, 1:5 and 1:10. A sample buffer similar to that described in EXAMPLE 7 may be used but appropriate concentrations should be used. For example, a 2× concentrated sample buffer should be used to prepare a 1:1 sample buffer to sample dilution. The resulting sample solution can be used for detection of beta lactamase activity and its resistance to beta lactamase inhibitor as described in EXAMPLE 9.

It is understood that individuals skilled in the art will recognize and be able to derive, through routine experimentation, many equivalents to the specific embodiments and examples of the present invention. For example, both reagent mixes may contain the enzyme inhibitor, albeit at different concentrations, so long as the inhibitor concentrations in the two reagent mixes are distinct and enable signal ratio distinction between inhibitor resistant and susceptible enzymes. Further examples include an assay comprising four or more reactions, one of which contains no enzyme inhibitor whereas each of the other reagent mixes contains a distinct enzyme inhibitor.

From the careful consideration of the foregoing description in light of the references cited herein, one skilled in the art can ascertain the essential characteristics of this invention and, without departing from the spirit and scope thereof, can make various changes and modifications of the invention to adapt it to various usages and conditions.

All publications, patents, patent applications and other citations mentioned in this patent are herein incorporated for the purpose of referencing only.

I claim:

1. A method for detecting the resistance or susceptibility of an enzyme to an inhibitor, comprising:
    a) contacting said enzyme to a first and a second reagent mixes substantially simultaneously each comprising a substrate that is processed by said enzyme to yield a detectable signal, wherein said first reagent mix contains no inhibitor while said second reagent mix contains an inhibitor of said enzyme at a concentration effective to inhibit said enzyme;
    b) incubating each reagent mix for substantially the same period, and
    c) at said substantially same period for each mix detecting a first signal intensity from the first reagent mix without the inhibitor and detecting a second signal intensity from the second reagent mix with the inhibitor, wherein the detection of the first signal intensity occurs at a single time frame only and is quantified to produce a single data point and the detection of the second signal intensity occurs at a single time frame only and is quantified to produce a single data point; and
    d) calculating a signal ratio (R-factor) which is a ratio of said two single data points or a multiple thereof; wherein the R-factor value indicates the resistance or susceptibility of an enzyme to an inhibitor, and wherein the process for calculating the R-factor is not repeated with varying multiple inhibitor concentrations for determination of an $IC_{50}$ value.

2. The method according to claim 1, wherein said substrate is a chromogenic substrate, a fluorogenic substrate, a chemiluminescent substrate or a biochemiluminescent substrate.

3. The method according to claim 2, wherein said chemiluminescent substrate is a dioxetane or a derivative thereof.

4. The method according to claim 2, wherein said biochemiluminescent substrate is a luciferin or a derivative thereof.

5. The method according to claim 1, wherein said enzyme is influenza viral neuraminidase, the substrate is an influenza viral neuraminidase substrate for detection of influenza viral neuraminidase activity and the inhibitor is an inhibitor of influenza viral neuraminidase.

6. The method according to claim 5, wherein the inhibitor is oseltamivir carboxylate, zanamivir, peramivir or laninamivir.

7. The method according to claim 1, wherein said enzyme is a beta lactamase, said substrate is a beta lactamase substrate for detection of beta lactamase activity and the inhibitor is an inhibitor of beta lactamase.

8. The method according to claim 7, wherein the beta lactamase inhibitor is clavulanate, sulbactam, tazobactam, avibactam, an ion chelator or a beta lactam antibiotic.

9. The method according to claim 8, wherein the beta lactamase antibiotic is an extended-spectrum cephalosporin, a carbapenem, an oxacillin or a derivative thereof.

10. The method according to claim 1, further comprising employing a resistance positive control sample comprising a mutant enzyme that exhibits resistance to said inhibitor optionally together with a resistance negative control sample comprising a wild-type enzyme that is susceptible to said inhibitor.

11. The method according to claim 10, comprising
    (e) determining a signal ratio which is a ratio of said second signal and said first signal or a multiple thereof in the negative control sample optionally together with determining said signal ratio in the positive control sample.

12. The method according to claim 11, wherein the enzyme is a neuraminidase, the inhibitor is oseltamivir carboxylate and the resistance positive control sample comprises a mutant H274Y strain that is resistant to said oseltamivir carboxylate.

13. The method according to claim 1, wherein the first signal intensity is equal to or above a cutoff for presence of said enzyme and, wherein an R-factor is defined as 10× (Reagent II Signal Intensity/Reagent I Signal Intensity), and wherein an R-Factor value equal to or above cutoff indicates resistance to said enzyme inhibitor and an R-factor below cutoff indicates susceptibility to said enzyme inhibitor.

14. The method according to claim 1, wherein the first signal intensity is equal to or above a cutoff for presence of said enzyme and an R-factor between 0.05 and 2.40 indicates susceptibility to said enzyme inhibitor and an R-factor of 2.41 to 10 indicates resistance to said enzyme inhibitor.

15. The method according to claim 1, wherein the second reagent mix contains an inhibitor of said enzyme at a concentration which is greater than cutoff value of $IC_{50}$ for said inhibitor.

16. The method according to claim 1, wherein said enzyme is a viral protease, the substrate is a substrate for detection of the viral protease activity and the inhibitor is an inhibitor of the viral protease.

17. The method according to claim 16, wherein said enzyme is HIV protease, the substrate is SEQ ID NO: 1 Fluorescein-Glu-Ser-Gln-Asn-Tyr-Pro-Ile-Val-Gln-Lys, where fluorescein is a fluorophore, and the inhibitor is nelfinavir.

18. The method according to claim 17, wherein the detectable signal comprises chromatographic detection of SEQ ID NO: 2 Fluorescein-Glu-Ser-Gln-Asn-Tyr and/or SEQ ID NO: 3 Pro-Ile-Val-Gln-Lys which are processed from SEQ ID NO: 1 Fluorescein-Glu-Ser-Gln-Asn-Tyr-Pro-Ile-Val-Gln-Lys substrate.

19. The method according to claim 1, comprising simultaneously detecting the resistance of an enzyme to a plurality of inhibitors.

20. The method according to claim 1, further comprising a third reagent mix, wherein the enzyme is influenza viral neuroaminidase, the inhibitor in the second reagent mix is oseltamivir and the third reagent mix contains the inhibitor zanamivir.

21. The method according to claim 1, wherein said enzyme is in a clinical sample.

22. The method according to claim 1, which consists essentially of steps a), b), c) and d).

23. The method according to claim 1, which consists of steps a), b), c) and d).

24. A method comprising:
   a) contacting an enzyme to a first and second reagent mixes each comprising a substrate that is processed by said enzyme to yield a detectable signal, wherein said first reagent mix contains no inhibitor while said second reagent mix contains an inhibitor of said enzyme at a concentration effective to inhibit said enzyme; and
   b) detecting a first signal intensity from the first reagent mix without the inhibitor and detecting a second signal intensity from the second reagent mix with the inhibitor with a signal detection device comprising a plurality of detection chambers to accommodate signal intensity detection of reactions in said first and second reagent mixes, wherein the detection of the first signal intensity occurs at a single time frame only and is quantified to produce a single data point and the detection of the second signal intensity occurs at a single time frame only and is quantified to produce a single data point; and
   c) calculating a signal ratio (R-factor) which is a ratio of said two single data points or a multiple thereof; wherein the R-factor value indicates the resistance or susceptibility of an enzyme to an inhibitor, and wherein the process for calculating the R-factor is not repeated with varying multiple inhibitor concentrations for determination of an $IC_{50}$ value.

25. The method according to claim 24, wherein said device is capable of detecting the signal intensities, determining the R-factor and further indicating the susceptibility or resistance of said enzyme to said inhibitor based on the R-factor.

26. The method according to claim 24, wherein each of said two detection chambers contains a signal sensor.

27. A method for detecting a carbapenemase-producing organism (CPO), comprising:
   a) preparing a sample in a sample solution containing ingredients capable of lysing or perforating bacterial cell wall and enabling carbapenemase activity;
   b) contacting the sample with a plurality of reagent mixes each comprising a substrate that is processed by a beta lactamase to yield a detectable signal intensity, wherein a first reagent mix contains no carbapenem while a second reagent mix contains a carbapenem at a concentration effective to inhibit the beta lactamase in a sample, and detecting a first signal intensity from the first reagent mix without carbapenem and detecting a second signal intensity from the second reagent mix with a carbapenem, wherein the detection of the first signal intensity occurs at a single time frame only and is quantified to produce a single data point and the detection of the second signal intensity occurs at a single time frame only and is quantified to produce a single data point; and
   c) calculating a signal ratio (R-factor) which is a ratio of said two single data points or a multiple thereof; wherein the R-factor value indicates the presence of a carbapenemase-producing organism, and wherein the process for calculating the R-factor is not repeated with varying multiple inhibitor concentrations for determination of an $IC_{50}$ value.

28. The method according to claim 27, wherein carbapenemase activity is detected when both the signal intensity of said first reagent and said R-factor are above cutoff values.

29. The method according to claim 27, wherein said sample is a single bacterial colony from a bacterial culture or a liquid bacterial culture.

30. A method for detecting the resistance or susceptibility of an enzyme to an inhibitor, comprising:
   a) contacting said enzyme to a first and a second reagent mixes substantially simultaneously each comprising a substrate that is processed by said enzyme to yield a detectable signal, wherein said first reagent mix contains no inhibitor while said second reagent mix contains an inhibitor of said enzyme at a concentration effective to inhibit said enzyme;
   b) incubating each reagent mix for substantially the same period, and
   c) at said substantially same period for each mix detecting a first light signal intensity from the first reagent mix without the inhibitor and detecting a second light signal intensity from the second reagent mix with the inhibitor, wherein the detection of the first light signal intensity occurs at a single time frame only and is quantified to produce a single data point and the detection of the second light signal intensity occurs at a single time frame only and is quantified to produce a single data point; and
   d) calculating a signal ratio (R-factor) which is a ratio of said two single data points or a multiple thereof; wherein the R-factor value indicates the resistance or susceptibility of an enzyme to an inhibitor, and wherein the process for calculating the R-factor is not repeated with varying multiple inhibitor concentrations for determination of an $IC_{50}$ value.

* * * * *

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fluorescein

<400> SEQUENCE: 1

Glu Ser Gln Asn Tyr Pro Ile Val Gln Lys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fluorescein
```

```
<400> SEQUENCE: 2

Glu Ser Gln Asn Tyr
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Ile Val Gln Lys
1               5
```